US008257953B2

(12) United States Patent
Lee et al.

(10) Patent No.: US 8,257,953 B2
(45) Date of Patent: Sep. 4, 2012

(54) HYPERTHERMOPHILIC DNA POLYMERASE AND METHODS OF PREPARATION THEREOF

(75) Inventors: Jung Hyun Lee, Seongnam Si (KR); Suk Tae Kwon, Suwon Si (KR); Sung Gyun Kang, Anyang Si (KR); Sang Jin Kim, Ansan Si (KR); Jung Ho Hyun, Seongnam Si (KR); Kae Kyoung Kwon, Ansan Si (KR); Yun Jae Kim, Ansan Si (KR); Hyun Sook Lee, Anyang Si (KR); Seung Seob Bae, Ansan Si (KR); Ki Hoon Nam, Suwon Si (KR); Jae Kyu Lim, Siheung Si (KR); Jung Ho Jeon, Ansan Si (KR); Sung Hyun Yang, Ansan Si (KR)

(73) Assignee: Korean Ocean Research & Development Institute, Ansan Si (KR)

( * ) Notice: Subject to any disclaimer, the term of this patent is extended or adjusted under 35 U.S.C. 154(b) by 737 days.

(21) Appl. No.: 12/089,587

(22) PCT Filed: Oct. 2, 2006

(86) PCT No.: PCT/KR2006/003988

§ 371 (c)(1),
(2), (4) Date: Sep. 10, 2008

(87) PCT Pub. No.: WO2007/043769

PCT Pub. Date: Apr. 19, 2007

(65) Prior Publication Data

US 2009/0148896 A1   Jun. 11, 2009

(30) Foreign Application Priority Data

Oct. 8, 2005  (KR) ........................ 10-2005-0094644

(51) Int. Cl.
*C12N 9/12*   (2006.01)
*C12N 15/11*   (2006.01)

(52) U.S. Cl. ........................ 435/194; 435/183; 536/23.1

(58) Field of Classification Search .................. None
See application file for complete search history.

(56) References Cited

OTHER PUBLICATIONS

Kim et al. Genbank Accession No. Q2Q453, Nov. 28, 2006.*
Lee et al., J. Bacteriol. 190:7491-7499(2008).*
Southworth et al. (Proc. Natl. Acad. Sci. USA, vol. 93, pp. 5281-5285, May 1996.*
Cambon-Bonavita et al., "Cloning, Expression, and Characterization of DNA Polymerase I from the Hyperthermophilic Archaea *Thermococcus fumicolans*," Extremophiles 4:215-225, 2000.
Hopfner et al., "Crystal Structure of a Thermostable Type B DNA Polymerase from *Thermococcus gorgonarius*," Proc. Natl. Acad. Sci. U.S.A. 96:3600-3605, 1999.
Takagi et al., "Characterization of DNA Polymerase from *Pyrococcus* sp. Strain KOD1 and its Application to PCR," Appl. Environ. Microbiol. 63:4504-4510, 1997.
Uemori et al., "A Novel DNA Polymerase in the Hyperthermophilic Archaeon, *Pyrococcus furiosus*: Gene Cloning, Expression, and Characterization," Genes to Cells 2:499-512, 1997.
International Search Report, International Application No. PCT/KR2006/003988, dated Jan. 9, 2007.
Cho et al., "Characterization of a dUTPase from the Hyperthermophilic Archaeon *Thermococcus onnurineus* NA1 and its Application in Polymerase Chain Reaction Amplification," Marine Biotechnol. 9:450-458, 2007.
Kim et al., "Characterization of a dITPase from the Hyperthermophilic Archaeon *Thermococcus onnurineus* NA1 and its Application in PCR Amplification," Appl. Microbiol. Biotechnol. 79:571-578, 2008.
Kim et al., "Cloning, Purification, and Characterization of a New DNA Polymerase from a Hyperthermophilic Archaeon, *Thermococcus* sp. NA1," J. Microbiol. Biotechnol. 17:1090-1097, 2007.
Kim et al., "Sensing Domain and Extension Rate of a Family B-Type DNA Polymerase Determine the Stalling at a Deaminated Base," J. Microbiol. Biotechnol. 18:1377-1385, 2008.

* cited by examiner

*Primary Examiner* — Richard Hutson
(74) *Attorney, Agent, or Firm* — Clark & Elbing LLP

(57) ABSTRACT

The present invention relates to a hyperthermophilic DNA polymerase and a preparation method thereof. The invention provides a novel hyperthermophilic DNA polymerase isolated from a *Thermococcus* sp. strain, a functional equivalent thereof, a protein having the amino acid sequence thereof, and a preparation method thereof. The DNA polymerase according to the invention is a DNA polymerase, which is hyperthermophilic and has an elongation ability and fidelity higher than those of prior commercial DNA polymerases. Thus, the DNA polymerase according to the invention will be useful in precision analysis, precision diagnosis, identification and the like, which require accurate PCR.

3 Claims, 8 Drawing Sheets

SEQUENCE LISTING

<160> NUMBER OF SEQ ID NOS: 19

<210> SEQ ID NO 1
<211> LENGTH: 2322
<212> TYPE: DNA
<213> ORGANISM: Thermococcus sp.

<400> SEQUENCE: 1

| | | | | | | |
|---|---|---|---|---|---|---|
| atgatcctcg | acgtcgatta | catcacagag | gacggaaagc | ctgtcatcag | gatcttcaag | 60 |
| aaggagaagg | gtgagttcaa | gattgaatac | gacagagact | tcgagcctta | catctatgca | 120 |
| ctcctcaagg | acgattctgc | catcgaggaa | gtgaagaaga | taaccgcgga | gcgccatgga | 180 |
| aaggttgtca | aggtcaagcg | tgccgagaag | gtgaataaga | agttcctcgg | ccgaccggtt | 240 |
| gaggtatgga | agctctactt | cgagcacccg | caggacgtgc | cgcaatccg | cgacaagata | 300 |
| agggctcacc | cgggggttat | cgacatttac | gagtacgaca | tacccttcgc | caagcgctac | 360 |
| ctcatagaca | agggcctcgt | ccccatggag | ggcgatgaag | aactgaagat | gctcgccttt | 420 |
| gacatcgaga | cgctctacca | cgagggcgag | gagttcggaa | ccgggcccat | actcatgata | 480 |
| agctacgcg | atgagaacga | ggcgagggtt | ataacctgga | aaaagataga | cctgccctac | 540 |
| gttgacgtcg | tctcaaccga | gaaggagatg | ataaagcgct | ttttgagggt | tgttaaggag | 600 |
| aaggatcctg | atgttctcat | tacctacaac | ggcgacaact | ttgactttgc | ttacctcaaa | 660 |
| aaacgttgcg | aaaagcttgg | gataagcttt | accctcgggc | gggacggaag | cgagccgaag | 720 |
| atacaccgca | tgggcgaccg | cttcgccgtg | gaggttaagg | ggaggattca | ttttgatctc | 780 |
| tatccggtca | taaggcgtac | catcaacctg | ccgacctaca | cccttgaggt | tgtttatgag | 840 |
| gcggtctttg | gcaaacccaa | ggagaaggta | tacgcggagg | agataaccct | tgcctgggag | 900 |
| agcggcgagg | ggcttgagcg | cgttgcgcgc | tactctatgg | aagatgcaaa | ggcaacctat | 960 |
| gagctcggaa | gagagttctt | cccgatggag | gcccagcttt | cgaggctgat | aggccagagc | 1020 |
| ctctgggacg | tgtcgcgttc | cagcaccggc | aacctcgtgg | agtggtttct | cctgcggaag | 1080 |
| gcctacgaga | ggaacgaact | tgcccccaac | aagccagacg | aggggagtt | agcgaggaga | 1140 |
| aggaacagtt | acgccggcgg | ctacgttaag | gaaccagaac | ggggattatg | ggacaatatt | 1200 |
| gtgtatttag | attttcgctc | tctttacccc | tcgatcataa | tcacccacaa | cgtctcgccg | 1260 |
| gatactctca | acagagaggg | ctgcaaggaa | tatgacgtcg | cccctcaggt | cggtcacaag | 1320 |
| ttctgcaagg | acttccccgg | cttcattccg | agccttctcg | ggaacctgct | cgaagagagg | 1380 |
| cagaagataa | agaggaagat | gaaggctaca | atagatcccc | tggagaagaa | gctcctcgac | 1440 |
| tacaggcagc | gggcaataaa | aatcttagcg | aacagctatt | acgggtacta | cggctatccc | 1500 |
| agggcaaggt | ggtactgcaa | ggagtgcgct | gagagcgtta | ccgcctgggg | cagggaatac | 1560 |
| attgagatga | cgataaggga | aattgaggag | aaatatggct | ttaaagtgct | gtatgcggac | 1620 |
| accgatggct | tttatgctac | aataccggga | gcggacgctg | aaactgtcaa | aaagaaggct | 1680 |
| aaagagttcc | ttaaatacat | aaatgccaag | ctgcctggat | tacttgagct | tgagtacgag | 1740 |
| ggcttctaca | agcgcggctt | cttcgtcacc | aaaaagaagt | acgctgttat | cgacgaggag | 1800 |
| ggcaagatcg | taactcgtgg | gctggagata | gtcaggcgtg | attggagtga | tatagctaaa | 1860 |
| gaaacacagg | ctagggttct | tgaggctctc | ctgaaggacg | gtaatgtaga | gaaggccgtt | 1920 |
| aagatagtca | aggagataac | cgagaagctg | agcaagtacg | aaatcccgcc | ggagaagctc | 1980 |

```
gtcatccacg agcagataac ccgcgagctg aaggactaca aagcaacggg cccgcacgta      2040
gcgatagcaa agcgtttggc ggcgagggga ataaaagttc gccccggcac gataatcagc      2100
tacatcgtcc ttaagggaag tggaaggata ggtgacaggg cgataccctt cgacgagttc      2160
gacccaacga agcacaagta cgacgctgac tactacatcg agaaccaggt tctcccggct      2220
gtgatgagga ttttggaggc gtttgggtat aagaagagg atttaagata ccagaagacg       2280
aggcaggttg gattgggggc ttggttgaag ccgaagaaat ga                          2322
```

```
<210> SEQ ID NO 2
<211> LENGTH: 773
<212> TYPE: PRT
<213> ORGANISM: Thermococcus sp.

<400> SEQUENCE: 2

Met Ile Leu Asp Val Asp Tyr Ile Thr Glu Asp Gly Lys Pro Val Ile
1               5                   10                  15

Arg Ile Phe Lys Lys Glu Lys Gly Glu Phe Lys Ile Glu Tyr Asp Arg
            20                  25                  30

Asp Phe Glu Pro Tyr Ile Tyr Ala Leu Leu Lys Asp Asp Ser Ala Ile
        35                  40                  45

Glu Glu Val Lys Lys Ile Thr Ala Glu Arg His Gly Lys Val Val Lys
    50                  55                  60

Val Lys Arg Ala Glu Lys Val Asn Lys Lys Phe Leu Gly Arg Pro Val
65                  70                  75                  80

Glu Val Trp Lys Leu Tyr Phe Glu His Pro Gln Asp Val Pro Ala Ile
                85                  90                  95

Arg Asp Lys Ile Arg Ala His Pro Gly Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Glu Asn Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Lys Glu Lys Asp Pro Asp Val Leu Ile Thr
            195                 200                 205

Tyr Asn Gly Asp Asn Phe Asp Phe Ala Tyr Leu Lys Lys Arg Cys Glu
        210                 215                 220

Lys Leu Gly Ile Ser Phe Thr Leu Gly Arg Asp Gly Ser Glu Pro Lys
225                 230                 235                 240

Ile His Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Val Val Tyr Glu Ala Val Phe Gly Lys Pro Lys Glu
        275                 280                 285

Lys Val Tyr Ala Glu Glu Ile Thr Leu Ala Trp Glu Ser Gly Glu Gly
    290                 295                 300

Leu Glu Arg Val Ala Arg Tyr Ser Met Glu Asp Ala Lys Ala Thr Tyr
305                 310                 315                 320
```

-continued

Glu Leu Gly Arg Glu Phe Phe Pro Met Glu Ala Gln Leu Ser Arg Leu
               325                 330                 335

Ile Gly Gln Ser Leu Trp Asp Val Ser Arg Ser Ser Thr Gly Asn Leu
           340                 345                 350

Val Glu Trp Phe Leu Leu Arg Lys Ala Tyr Glu Arg Asn Glu Leu Ala
           355                 360                 365

Pro Asn Lys Pro Asp Glu Gly Glu Leu Ala Arg Arg Arg Asn Ser Tyr
       370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
               405                 410                 415

Asn Val Ser Pro Asp Thr Leu Asn Arg Glu Gly Cys Lys Glu Tyr Asp
           420                 425                 430

Val Ala Pro Gln Val Gly His Lys Phe Cys Lys Asp Phe Pro Gly Phe
       435                 440                 445

Ile Pro Ser Leu Leu Gly Asn Leu Leu Glu Glu Arg Gln Lys Ile Lys
   450                 455                 460

Arg Lys Met Lys Ala Thr Ile Asp Pro Leu Glu Lys Lys Leu Leu Asp
465                 470                 475                 480

Tyr Arg Gln Arg Ala Ile Lys Ile Leu Ala Asn Ser Tyr Tyr Gly Tyr
               485                 490                 495

Tyr Gly Tyr Pro Arg Ala Arg Trp Tyr Cys Lys Glu Cys Ala Glu Ser
           500                 505                 510

Val Thr Ala Trp Gly Arg Glu Tyr Ile Glu Met Thr Ile Arg Glu Ile
       515                 520                 525

Glu Glu Lys Tyr Gly Phe Lys Val Leu Tyr Ala Asp Thr Asp Gly Phe
   530                 535                 540

Tyr Ala Thr Ile Pro Gly Ala Asp Ala Glu Thr Val Lys Lys Lys Ala
545                 550                 555                 560

Lys Glu Phe Leu Lys Tyr Ile Asn Ala Lys Leu Pro Gly Leu Leu Glu
               565                 570                 575

Leu Glu Tyr Glu Gly Phe Tyr Lys Arg Gly Phe Phe Val Thr Lys Lys
           580                 585                 590

Lys Tyr Ala Val Ile Asp Glu Glu Gly Lys Ile Val Thr Arg Gly Leu
       595                 600                 605

Glu Ile Val Arg Arg Asp Trp Ser Asp Ile Ala Lys Glu Thr Gln Ala
   610                 615                 620

Arg Val Leu Glu Ala Leu Leu Lys Asp Gly Asn Val Glu Lys Ala Val
625                 630                 635                 640

Lys Ile Val Lys Glu Ile Thr Glu Lys Leu Ser Lys Tyr Glu Ile Pro
               645                 650                 655

Pro Glu Lys Leu Val Ile His Glu Gln Ile Thr Arg Glu Leu Lys Asp
           660                 665                 670

Tyr Lys Ala Thr Gly Pro His Val Ala Ile Ala Lys Arg Leu Ala Ala
       675                 680                 685

Arg Gly Ile Lys Val Arg Pro Gly Thr Ile Ile Ser Tyr Ile Val Leu
   690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Asp Tyr Tyr Ile Glu Asn Gln
               725                 730                 735

Val Leu Pro Ala Val Met Arg Ile Leu Glu Ala Phe Gly Tyr Lys Lys
           740                 745                 750

Glu Asp Leu Arg Tyr Gln Lys Thr Arg Gln Val Gly Leu Gly Ala Trp
    755                 760                 765

Leu Lys Pro Lys Lys
    770

<210> SEQ ID NO 3
<211> LENGTH: 3927
<212> TYPE: DNA
<213> ORGANISM: Thermococcus sp.

<400> SEQUENCE: 3

| | | | | | |
|---|---|---|---|---|---|
| atgatcctcg | acgtcgatta | catcacagag | gacggaaagc | ctgtcatcag | gatcttcaag | 60 |
| aaggagaagg | gtgagttcaa | gattgaatac | gacagagact | tcgagcctta | catctatgca | 120 |
| ctcctcaagg | acgattctgc | catcgaggaa | gtgaagaaga | taaccgcgga | gcgccatgga | 180 |
| aaggttgtca | aggtcaagcg | tgccgagaag | gtgaataaga | agttcctcgg | ccgaccggtt | 240 |
| gaggtatgga | agctctactt | cgagcacccg | caggacgtgc | ccgcaatccg | cgacaagata | 300 |
| agggctcacc | cgggggttat | cgacatttac | gagtacgaca | tacccttcgc | caagcgctac | 360 |
| ctcatagaca | agggcctcgt | ccccatggag | ggcgatgaag | aactgaagat | gctcgccttt | 420 |
| gacatcgaga | cgctctacca | cgagggcgag | gagttcggaa | ccgggcccat | actcatgata | 480 |
| agctacgcgg | atgagaacga | ggcgagggtt | ataacctgga | aaaagataga | cctgccctac | 540 |
| gttgacgtcg | tctcaaccga | gaaggagatg | ataaagcgct | ttttgagggt | tgttaaggag | 600 |
| aaggatcctg | atgttctcat | tacctacaac | ggcgacaact | tgactttgc | ttacctcaaa | 660 |
| aaacgttgcg | aaaagcttgg | gataagcttt | accctcgggc | gggacggaag | cgagccgaag | 720 |
| atacaccgca | tgggcgaccg | cttcgccgtg | gaggttaagg | ggaggattca | ttttgatctc | 780 |
| tatccggtca | taaggcgtac | catcaacctg | ccgacctaca | cccttgaggt | tgtttatgag | 840 |
| gcggtctttg | gcaaacccaa | ggagaaggta | tacgcggagg | agataaccct | tgcctgggag | 900 |
| agcggcgagg | ggcttgagcg | cgttgcgcgc | tactctatgg | aagatgcaaa | ggcaacctat | 960 |
| gagctcggaa | gagagttctt | cccgatggag | gcccagcttt | cgaggctgat | aggccagagc | 1020 |
| ctctgggacg | tgtcgcgttc | cagcaccggc | aacctcgtgg | agtggttct | cctgcggaag | 1080 |
| gcctacgaga | ggaacgaact | tgcccccaac | aagccagacg | aggggagtt | agcgaggaga | 1140 |
| aggaacagtt | acgccggcgg | ctacgttaag | gaaccagaac | ggggattatg | gacaatattt | 1200 |
| gtgtatttag | attttcgctc | tctttacccc | tcgatcataa | tcacccacaa | cgtctcgccg | 1260 |
| gatactctca | acagagaggg | ctgcaaggaa | tatgacgtcg | cccctcaggt | cggtcacaag | 1320 |
| ttctgcaagg | acttccccgg | cttcattccg | agccttctcg | gaacctgct | cgaagagagg | 1380 |
| cagaagataa | agaggaagat | gaaggctaca | atagatcccc | tggagaagaa | gctcctcgac | 1440 |
| tacaggcagc | gggcaataaa | aatcttagcg | aatagcattc | tacccgatga | atgggttcct | 1500 |
| ttgctcattg | atggaaggct | caaactgacg | agaatcggcg | attttgttga | taatgcgatg | 1560 |
| gatgagggga | accccctaaa | gagcaatgaa | accgaggttc | tcgaagtttt | ggggataaat | 1620 |
| gccatttcct | tcaacagaaa | gacaaagata | tccgaggtaa | ggcccgtcag | agcccttata | 1680 |
| cggcaccgct | atcgcggaaa | agtgtacagc | ataaaactct | cctccggcag | gaaaatcaag | 1740 |
| gtcacggagg | ggcacagtct | tttcacagtc | aaaaatgggg | aacttgtgga | agttaccggc | 1800 |
| gggaaagtaa | aacctgggga | cttcatagca | gttccaagga | ggattaacct | cccggaaagg | 1860 |
| catgagagga | taaccttgc | cgatgttctc | ctcaaccttc | tgaggagga | aaccgccgac | 1920 |
| gtcgtcttaa | ctataccac | caaggggcgc | aagaacttct | ttagggcat | gctgagaacc | 1980 |

```
ctccgctgga tttttgaggg agagaaaaga cccagaacgg cccgaagata cctcgaacac    2040
ctccaaaagc tgggctatgt cagactcaaa aaaatcggct acgaagttct tgatgagaaa    2100
gctttaagga aatacagggc gctctacgag gttcttgctg aaaaggttag gtacaacggc    2160
aacaagaggg aatacctggt tgcctttaac gacctcaggg ataagataga gtttatgccg    2220
gaggaagagc ttagggagtg gaagattgga accctcaacg gctttaggat ggagcctttc    2280
attgaagtca acgaagacct tgcaaagctt ctcggttatt acgtcagcga gggttatgca    2340
ggaaagcaga ggaaccagaa gaacgggtgg agctattcgg tcaagcttta caacaatgac    2400
cagaaggttc tcgatgacat ggaaaggctt gcatcgaaat tcttcggaaa ggtgagacgc    2460
ggaaagaact acgtggagat gcccaagaaa atggcctacg tgctcttcaa gagcctatgt    2520
ggtacgctgg cggagaacaa acgagttcct gaggttatat tcacatcccc cgaaaacgtg    2580
cgctgggcct ttttagaggg gtacttcata ggggacggcg acctccatcc gagcaagagg    2640
gttaggcttt ccacaaaaag cgagacctta gtcaacggtt tgataatcct cctcaactcc    2700
cttggcatct cggccgttaa gataaggttt gagagcgggg tgtacagagt tctagttaac    2760
gaagaactat cgttccttgg caacagcaag aagaagaacg cctattactc tcacgtaatt    2820
ccaaaggaga tactcgaaga cgtcttcgaa aagaggtttc agaaaaacgt gagccccaaa    2880
aagcttagag agaagattaa gaggggcgaa cttaaccagg agaaggccaa gagaattttcc   2940 tggcttctcg agggagacat tgtgcttgac agagttgaag aagtcgaagt tgaggactac    3000
aacggctacg tctacgatct aagcgttgag gagaatgaaa acttcctggc aggatttgga    3060
atgatatacg ctcacaacag ctattacggg tactacggct atcccagggc aaggtggtac    3120
tgcaaggagt gcgctgagag cgttaccgcc tggggcaggg aatacattga gatgacgata    3180
agggaaattg aggagaaata tggctttaaa gtgctgtatg cggacaccga tggctttttat   3240 gctacaatac cgggagcgga cgctgaaact gtcaaaaaga aggctaaaga gttccttaaa    3300
tacataaatg ccaagctgcc tggattactt gagcttgagt acgagggctt ctacaagcgc    3360
ggcttcttcg tcaccaaaaa gaagtacgct gttatcgacg aggagggcaa gatcgtaact    3420
cgtgggctgg agatagtcag gcgtgattgg agtgatatag ctaaagaaac acaggctagg    3480
gttcttgagg ctctcctgaa ggacggtaat gtagagaagg ccgttaagat agtcaaggag    3540
ataaccgaga agctgagcaa gtacgaaatc ccgccggaga gctcgtcat ccacgagcag     3600 ataacccgcg agctgaagga ctacaaagca acgggcccgc acgtagcgat agcaaagcgt    3660
ttggcggcga gggaataaa agttcgcccc ggcacgataa tcagctacat cgtccttaag    3720
ggaagtggaa ggataggtga cagggcgata cccttcgacg agttcgaccc aacgaagcac    3780
aagtacgacg ctgactacta catcgagaac caggttctcc cggctgtgat gaggattttg    3840
gaggcgtttg ggtataagaa agaggattta agataccaga gacgaggca ggttggattg     3900 ggggcttggt tgaagccgaa gaaatga                                        3927

<210> SEQ ID NO 4
<211> LENGTH: 1308
<212> TYPE: PRT
<213> ORGANISM: Thermococcus sp.

<400> SEQUENCE: 4

Met Ile Leu Asp Val Asp Tyr Ile Thr Glu Asp Gly Lys Pro Val Ile
1               5                   10                  15

Arg Ile Phe Lys Lys Glu Lys Gly Glu Phe Lys Ile Glu Tyr Asp Arg
            20                  25                  30
```

-continued

```
Asp Phe Glu Pro Tyr Ile Tyr Ala Leu Leu Lys Asp Ser Ala Ile
         35                  40                  45
Glu Glu Val Lys Lys Ile Thr Ala Arg His Gly Lys Val Val Lys
 50                  55                  60
Val Lys Arg Ala Glu Lys Val Asn Lys Phe Leu Gly Arg Pro Val
 65                  70                  75                  80
Glu Val Trp Lys Leu Tyr Phe Glu His Pro Gln Asp Val Pro Ala Ile
                 85                  90                  95
Arg Asp Lys Ile Arg Ala His Pro Gly Val Ile Asp Ile Tyr Glu Tyr
                100                 105                 110
Asp Ile Pro Phe Ala Lys Arg Tyr Leu Ile Asp Lys Gly Leu Val Pro
                115                 120                 125
Met Glu Gly Asp Glu Leu Lys Met Leu Ala Phe Asp Ile Glu Thr
130                 135                 140
Leu Tyr His Glu Gly Glu Phe Gly Thr Gly Pro Ile Leu Met Ile
145                 150                 155                 160
Ser Tyr Ala Asp Glu Asn Glu Ala Arg Val Ile Thr Trp Lys Lys Ile
                165                 170                 175
Asp Leu Pro Tyr Val Asp Val Ser Thr Glu Lys Glu Met Ile Lys
                180                 185                 190
Arg Phe Leu Arg Val Val Lys Glu Lys Asp Pro Asp Val Leu Ile Thr
                195                 200                 205
Tyr Asn Gly Asp Asn Phe Asp Phe Ala Tyr Leu Lys Lys Arg Cys Glu
                210                 215                 220
Lys Leu Gly Ile Ser Phe Thr Leu Gly Arg Asp Gly Ser Glu Pro Lys
225                 230                 235                 240
Ile His Arg Met Gly Asp Arg Phe Ala Val Glu Val Lys Gly Arg Ile
                245                 250                 255
His Phe Asp Leu Tyr Pro Val Ile Arg Arg Thr Ile Asn Leu Pro Thr
                260                 265                 270
Tyr Thr Leu Glu Val Val Tyr Glu Ala Val Phe Gly Lys Pro Lys Glu
                275                 280                 285
Lys Val Tyr Ala Glu Glu Ile Thr Leu Ala Trp Glu Ser Gly Glu Gly
290                 295                 300
Leu Glu Arg Val Ala Arg Tyr Ser Met Glu Asp Ala Lys Ala Thr Tyr
305                 310                 315                 320
Glu Leu Gly Arg Glu Phe Phe Pro Met Glu Ala Gln Leu Ser Arg Leu
                325                 330                 335
Ile Gly Gln Ser Leu Trp Asp Val Ser Arg Ser Ser Thr Gly Asn Leu
                340                 345                 350
Val Glu Trp Phe Leu Leu Arg Lys Ala Tyr Glu Arg Asn Glu Leu Ala
                355                 360                 365
Pro Asn Lys Pro Asp Glu Gly Glu Leu Ala Arg Arg Asn Ser Tyr
370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
                420                 425                 430
Val Ala Pro Gln Val Gly His Lys Phe Cys Lys Asp Phe Pro Gly Phe
                435                 440                 445
Ile Pro Ser Leu Leu Gly Asn Leu Leu Glu Glu Arg Gln Lys Ile Lys
450                 455                 460
```

-continued

Arg Lys Met Lys Ala Thr Ile Asp Pro Leu Glu Lys Leu Leu Asp
465                 470                 475                 480

Tyr Arg Gln Arg Ala Ile Lys Ile Leu Ala Asn Ser Ile Leu Pro Asp
            485                 490                 495

Glu Trp Val Pro Leu Leu Ile Asp Gly Arg Leu Lys Leu Thr Arg Ile
            500                 505                 510

Gly Asp Phe Val Asp Asn Ala Met Asp Glu Gly Asn Pro Leu Lys Ser
            515                 520                 525

Asn Glu Thr Glu Val Leu Glu Val Leu Gly Ile Asn Ala Ile Ser Phe
530                 535                 540

Asn Arg Lys Thr Lys Ile Ser Glu Val Arg Pro Val Arg Ala Leu Ile
545                 550                 555                 560

Arg His Arg Tyr Arg Gly Lys Val Tyr Ser Ile Lys Leu Ser Ser Gly
                565                 570                 575

Arg Lys Ile Lys Val Thr Glu Gly His Ser Leu Phe Thr Val Lys Asn
            580                 585                 590

Gly Glu Leu Val Glu Val Thr Gly Lys Val Lys Pro Gly Asp Phe
            595                 600                 605

Ile Ala Val Pro Arg Arg Ile Asn Leu Pro Glu Arg His Glu Arg Ile
610                 615                 620

Asn Leu Ala Asp Val Leu Leu Asn Leu Pro Glu Glu Thr Ala Asp
625                 630                 635                 640

Val Val Leu Thr Ile Pro Thr Lys Gly Arg Lys Asn Phe Phe Arg Gly
                645                 650                 655

Met Leu Arg Thr Leu Arg Trp Ile Phe Glu Gly Glu Lys Arg Pro Arg
            660                 665                 670

Thr Ala Arg Arg Tyr Leu Glu His Leu Gln Lys Leu Gly Tyr Val Arg
            675                 680                 685

Leu Lys Lys Ile Gly Tyr Glu Val Leu Asp Glu Lys Ala Leu Arg Lys
            690                 695                 700

Tyr Arg Ala Leu Tyr Glu Val Leu Ala Glu Lys Val Arg Tyr Asn Gly
705                 710                 715                 720

Asn Lys Arg Glu Tyr Leu Val Ala Phe Asn Asp Leu Arg Asp Lys Ile
            725                 730                 735

Glu Phe Met Pro Glu Glu Glu Leu Arg Glu Trp Lys Ile Gly Thr Leu
            740                 745                 750

Asn Gly Phe Arg Met Glu Pro Phe Ile Glu Val Asn Glu Asp Leu Ala
            755                 760                 765

Lys Leu Leu Gly Tyr Tyr Val Ser Glu Gly Tyr Ala Gly Lys Gln Arg
770                 775                 780

Asn Gln Lys Asn Gly Trp Ser Tyr Ser Val Lys Leu Tyr Asn Asn Asp
785                 790                 795                 800

Gln Lys Val Leu Asp Asp Met Glu Arg Leu Ala Ser Lys Phe Phe Gly
            805                 810                 815

Lys Val Arg Arg Gly Lys Asn Tyr Val Glu Met Pro Lys Lys Met Ala
            820                 825                 830

Tyr Val Leu Phe Lys Ser Leu Cys Gly Thr Leu Ala Glu Asn Lys Arg
            835                 840                 845

Val Pro Glu Val Ile Phe Thr Ser Pro Glu Asn Val Arg Trp Ala Phe
850                 855                 860

Leu Glu Gly Tyr Phe Ile Gly Asp Gly Asp Leu His Pro Ser Lys Arg
865                 870                 875                 880

Val Arg Leu Ser Thr Lys Ser Glu Thr Leu Val Asn Gly Leu Ile Ile
                885                 890                 895

-continued

Leu Leu Asn Ser Leu Gly Ile Ser Ala Val Lys Ile Arg Phe Glu Ser
                900                 905                 910

Gly Val Tyr Arg Val Leu Val Asn Glu Glu Leu Ser Phe Leu Gly Asn
            915                 920                 925

Ser Lys Lys Lys Asn Ala Tyr Tyr Ser His Val Ile Pro Lys Glu Ile
        930                 935                 940

Leu Glu Asp Val Phe Glu Lys Arg Phe Gln Lys Asn Val Ser Pro Lys
945                 950                 955                 960

Lys Leu Arg Glu Lys Ile Lys Arg Gly Glu Leu Asn Gln Glu Lys Ala
                965                 970                 975

Lys Arg Ile Ser Trp Leu Leu Glu Gly Asp Ile Val Leu Asp Arg Val
            980                 985                 990

Glu Glu Val Glu Val Glu Asp Tyr Asn Gly Tyr Val Tyr Asp Leu Ser
        995                 1000                1005

Val Glu Glu Asn Glu Asn Phe Leu Ala Gly Phe Gly Met Ile Tyr
    1010            1015                1020

Ala His Asn Ser Tyr Tyr Gly Tyr Tyr Gly Tyr Pro Arg Ala Arg
    1025            1030                1035

Trp Tyr Cys Lys Glu Cys Ala Glu Ser Val Thr Ala Trp Gly Arg
    1040            1045                1050

Glu Tyr Ile Glu Met Thr Ile Arg Glu Ile Glu Lys Tyr Gly
    1055            1060                1065

Phe Lys Val Leu Tyr Ala Asp Thr Asp Gly Phe Tyr Ala Thr Ile
    1070            1075                1080

Pro Gly Ala Asp Ala Glu Thr Val Lys Lys Lys Ala Lys Glu Phe
    1085            1090                1095

Leu Lys Tyr Ile Asn Ala Lys Leu Pro Gly Leu Leu Glu Leu Glu
    1100            1105                1110

Tyr Glu Gly Phe Tyr Lys Arg Gly Phe Phe Val Thr Lys Lys Lys
    1115            1120                1125

Tyr Ala Val Ile Asp Glu Glu Gly Lys Ile Val Thr Arg Gly Leu
    1130            1135                1140

Glu Ile Val Arg Arg Asp Trp Ser Asp Ile Ala Lys Glu Thr Gln
    1145            1150                1155

Ala Arg Val Leu Glu Ala Leu Leu Lys Asp Gly Asn Val Glu Lys
    1160            1165                1170

Ala Val Lys Ile Val Lys Glu Ile Thr Glu Lys Leu Ser Lys Tyr
    1175            1180                1185

Glu Ile Pro Pro Glu Lys Leu Val Ile His Glu Gln Ile Thr Arg
    1190            1195                1200

Glu Leu Lys Asp Tyr Lys Ala Thr Gly Pro His Val Ala Ile Ala
    1205            1210                1215

Lys Arg Leu Ala Ala Arg Gly Ile Lys Val Arg Pro Gly Thr Ile
    1220            1225                1230

Ile Ser Tyr Ile Val Leu Lys Gly Ser Gly Arg Ile Gly Asp Arg
    1235            1240                1245

Ala Ile Pro Phe Asp Glu Phe Asp Pro Thr Lys His Lys Tyr Asp
    1250            1255                1260

Ala Asp Tyr Tyr Ile Glu Asn Gln Val Leu Pro Ala Val Met Arg
    1265            1270                1275

Ile Leu Glu Ala Phe Gly Tyr Lys Lys Glu Asp Leu Arg Tyr Gln
    1280            1285                1290

Lys Thr Arg Gln Val Gly Leu Gly Ala Trp Leu Lys Pro Lys Lys
    1295            1300                1305

```
<210> SEQ ID NO 5
<211> LENGTH: 39
<212> TYPE: DNA
<213> ORGANISM: Artificial Sequence
<220> FEATURE:
<223> OTHER INFORMATION: TNA-pol N-terminal sense primer

<400> SEQUENCE: 5
cgacccggca tatgatcctc gacgtcgatt acatcacag                               39

<210> SEQ ID NO 6
<211> LENGTH: 48
<212> TYPE: DNA
<213> ORGANISM: Artificial Sequence
<220> FEATURE:
<223> OTHER INFORMATION: TNA-pol N-terminal antisense primer

<400> SEQUENCE: 6
gccgtagtac ccgtaatagc tgttcgctaa gattttatt gcccgctg                      48

<210> SEQ ID NO 7
<211> LENGTH: 48
<212> TYPE: DNA
<213> ORGANISM: Artificial Sequence
<220> FEATURE:
<223> OTHER INFORMATION: TNA-pol C-terminal sense primer

<400> SEQUENCE: 7
cagcgggcaa taaaatctt agcgaacagc tattacgggt actacggc                      48

<210> SEQ ID NO 8
<211> LENGTH: 38
<212> TYPE: DNA
<213> ORGANISM: Artificial Sequence
<220> FEATURE:
<223> OTHER INFORMATION: TNA-pol C-terminal antisense primer

<400> SEQUENCE: 8
ctccacatct cgagtttctt cggcttcaac caagcccc                                38

<210> SEQ ID NO 9
<211> LENGTH: 39
<212> TYPE: DNA
<213> ORGANISM: Artificial Sequence
<220> FEATURE:
<223> OTHER INFORMATION: TNA-pol sense primer with restriction site

<400> SEQUENCE: 9
cgacccggca tatgatcctc gacgtcgatt acatcacag                               39

<210> SEQ ID NO 10
<211> LENGTH: 38
<212> TYPE: DNA
<213> ORGANISM: Artificial Sequence
<220> FEATURE:
<223> OTHER INFORMATION: TNA-pol antisense primer with restriction site

<400> SEQUENCE: 10
ctccacatct cgagtttctt cggcttcaac caagcccc                                38

<210> SEQ ID NO 11
<211> LENGTH: 25
<212> TYPE: DNA
<213> ORGANISM: Artificial Sequence
<220> FEATURE:
<223> OTHER INFORMATION: TNA-pol sense primer for 2kb amplification
```

-continued

```
<400> SEQUENCE: 11
actaaattgg tgataccgtt atgag                                        25

<210> SEQ ID NO 12
<211> LENGTH: 24
<212> TYPE: DNA
<213> ORGANISM: Artificial Sequence
<220> FEATURE:
<223> OTHER INFORMATION: TNA-pol antisense primer for 2 kb amplification

<400> SEQUENCE: 12
ggaacataaa atgtaaggga cttc                                         24

<210> SEQ ID NO 13
<211> LENGTH: 25
<212> TYPE: DNA
<213> ORGANISM: Artificial Sequence
<220> FEATURE:
<223> OTHER INFORMATION: TNA-pol sense primer for 2 and 4 kb
      amplification

<400> SEQUENCE: 13
actaaattgg tgataccgtt atgag                                        25

<210> SEQ ID NO 14
<211> LENGTH: 25
<212> TYPE: DNA
<213> ORGANISM: Artificial Sequence
<220> FEATURE:
<223> OTHER INFORMATION: TNA_pol antisense primer for 2 and 4 kb
      amplification

<400> SEQUENCE: 14
gtctctgatg ctcatgatgt agttc                                        25

<210> SEQ ID NO 15
<211> LENGTH: 25
<212> TYPE: DNA
<213> ORGANISM: Artificial Sequence
<220> FEATURE:
<223> OTHER INFORMATION: TNA_pol sense primer for 8 kb amplification

<400> SEQUENCE: 15
actaaattgg tgataccgtt atgag                                        25

<210> SEQ ID NO 16
<211> LENGTH: 25
<212> TYPE: DNA
<213> ORGANISM: Artificial Sequence
<220> FEATURE:
<223> OTHER INFORMATION: TNA_pol antisense primer for 8 kb amplification

<400> SEQUENCE: 16
gaggagctct ttagaattct caagc                                        25

<210> SEQ ID NO 17
<211> LENGTH: 774
<212> TYPE: PRT
<213> ORGANISM: Thermococcus Kodakarensis

<400> SEQUENCE: 17

Met Ile Leu Asp Thr Asp Tyr Ile Thr Glu Asp Gly Lys Pro Val Ile
1               5                   10                  15
Arg Ile Phe Lys Lys Glu Asn Gly Glu Phe Lys Ile Glu Tyr Asp Arg
            20                  25                  30
```

-continued

```
Thr Phe Glu Pro Tyr Phe Tyr Ala Leu Leu Lys Asp Asp Ser Ala Ile
    35                  40                  45

Glu Glu Val Lys Lys Ile Thr Ala Glu Arg His Gly Thr Val Val Thr
50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Val Pro Ala Ile
            85                  90                  95

Arg Asp Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Val Pro
        115                 120                 125

Met Glu Gly Asp Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
        180                 185                 190

Arg Phe Leu Arg Val Val Lys Glu Lys Asp Pro Asp Val Leu Ile Thr
    195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
        260                 265                 270

Tyr Thr Leu Glu Ala Val Tyr Glu Ala Val Phe Gly Gln Pro Lys Glu
    275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
        340                 345                 350

Val Glu Trp Phe Leu Leu Arg Lys Ala Tyr Glu Arg Asn Glu Leu Ala
    355                 360                 365

Pro Asn Lys Pro Asp Glu Lys Glu Leu Ala Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
        420                 425                 430

Val Ala Pro Gln Val Gly His Arg Phe Cys Lys Asp Phe Pro Gly Phe
    435                 440                 445

Ile Pro Ser Leu Leu Gly Asp Leu Leu Glu Glu Arg Gln Lys Ile Lys
450                 455                 460
```

```
Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770

<210> SEQ ID NO 18
<211> LENGTH: 775
<212> TYPE: PRT
<213> ORGANISM: Pyrococcus furiosus

<400> SEQUENCE: 18

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
    50                  55                  60
```

-continued

```
Ile Val Asp Val Glu Lys Val Glu Lys Phe Leu Gly Lys Pro Ile
 65                  70                  75                  80

Thr Val Trp Lys Leu Tyr Leu Glu His Pro Gln Asp Val Pro Thr Ile
                 85                  90                  95

Arg Glu Lys Val Arg Glu His Pro Ala Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495
```

```
Tyr Tyr Gly Tyr Ala Lys Ala Arg Trp Tyr Cys Lys Glu Cys Ala Glu
                500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
770                 775

<210> SEQ ID NO 19
<211> LENGTH: 775
<212> TYPE: PRT
<213> ORGANISM: Pyrococcus sp.

<400> SEQUENCE: 19

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
                20                  25                  30

Asn Phe Arg Pro Tyr Ile Tyr Ala Leu Leu Lys Asp Asp Ser Gln Ile
            35                  40                  45

Asp Glu Val Arg Lys Ile Thr Ala Glu Arg His Gly Lys Ile Val Arg
        50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95
```

-continued

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
    195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
            245                 250                 255

His Phe Asp Leu Tyr His Val Ile Arg Arg Thr Ile Asn Leu Pro Thr
        260                 265                 270

Tyr Thr Leu Glu Ala Val Tyr Glu Ala Ile Phe Gly Lys Pro Lys Glu
    275                 280                 285

Lys Val Tyr Ala His Glu Ile Ala Glu Ala Trp Glu Thr Gly Lys Gly
            290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

-continued

```
Leu Glu Glu Lys Phe Gly Phe Lys Val Leu Tyr Ile Asp Thr Asp Gly
            530                 535                 540

Leu Tyr Ala Thr Ile Pro Gly Ala Lys Pro Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
        755                 760                 765

Trp Leu Asn Ile Lys Lys Lys
770                 775
```

HYPERTHERMOPHILIC DNA POLYMERASE AND METHODS OF PREPARATION THEREOF

CROSS-REFERENCE TO RELATED APPLICATIONS

This application claims priority under 35 U.S.C. §371 from international application PCT/KR2006/003988, filed Oct.2, 2006, which claims priority from Korean Patent Application 10-2005-0094644, filed Oct. 8, 2005.

TECHNICAL FIELD

The recent advance of genomic research has produced vast amounts of sequence information. With a generally applicable combination of conventional genetic engineering and genomic research techniques, the genome sequences of some hyperthermophilic microorganisms are of considerable biotechnological interest due to heat-stable enzymes, and many extremely thermostable enzymes are being developed for biotechnological purposes.

PCR, which uses the thermostable DNA polymerase, is one of the most important contributions to protein and genetic research and is currently used in a broad array of biological applications. More than 50 DNA polymerase genes have been cloned from various organisms, including thermophiles and archaeas. Recently, family B DNA polymerases from hyperthermophilic archaea, *Pyrococcus* and *Thermococcus*, have been widely used since they have higher fidelity in PCR based on their proof reading activity than Taq polymerase commonly used. However, the improvement of the high fidelity enzyme has been on demand due to lower DNA elongation ability. The present inventors isolated a new hyperthermophilic strain from a deep-sea hydrothermal vent area at the PACMANUS field. It was identified as a member of *Thermococcus* based on 16S rDNA sequence analysis, and the whole genome sequencing is currently in process to search for many extremely thermostable enzymes. The analysis of the genome information displayed that the strain possessed a family B type DNA polymerase. The present inventors cloned the gene corresponding to the DNA polymerase was cloned and expressed in *E. coli*. In addition, the recombinant enzyme was purified and its enzymatic characteristics were examined.

Accordingly, the present inventors have isolated and prepared DNA polymerase from hyperthermophilic archaebacterium *Thermococcus* sp. NA1, thereby completing the present invention.

BACKGROUND ART

References relating to the background of the present invention are listed as follows:

[1] Saiki R K, Gelfand D H, Stoffel S, Higuchi R, Horn G, Mullis K B, Erlich H A. Primer-directed enzymatic amplification of DNA with a thermostable DNA polymerase. Science 1988; 239:487-491.

[2] Ito J, Braithwaite D K. Compilation and alignment of DNA polymerases. Nucleic Acids Res 1991; 19:4045-4057.

[3] Perler F B, Kumar S, Kong H. Thermostable DNA polymerases. Adv Protein Chem 1996; 48:377-435.

[4] Lundberg K S, Shoemaker D D, Adams M W, Short J M, Sorge J A, Mathur E J. High-fidelity amplification using a thermostable DNA polymerase isolated from *Pyrococcus furiosus*. Gene 1991; 108:1-6.

[5] Mattila P, Korpela J, Tenkanen T, Pitkanen K. Fidelity of DNA synthesis by the *Thermococcus litoralis* DNA polymerase—an extremely heat stable enzyme with proofreading activity. Nucleic Acids Res 1991; 19:4967-73.

[6] Kong H, Kucera R B, Jack W E. Characterization of a DNA polymerase from the hyperthermophile archaea *Thermococcus litoralis*. Vent DNA polymerase, steady state kinetics, thermal stability, processivity, strand displacement, and exonuclease activities. J Biol Chem 1993; 268:1965-1975.

[7] Southworth M W, Kong H, Kucera R B, Ware J, Jannasch H W, Perler F B. Cloning of thermostable DNA polymerases from hyperthermophilic marine Archaea with emphasis on *Thermococcus* sp. 9 degrees N-7 and mutations affecting 3'-5' exonuclease activity. Proc Natl Acad Sci USA. 1996; 93:5281-5285.

[8] Takagi M, Nishioka M, Kakihara H, Kitabayashi M, Inoue H, Kawakami B, Oka M, Imanaka T. Characterization of DNA polymerase from *Pyrococcus* sp. strain KOD1 and its application to PCR. Appl Environ Microbiol 1997; 63:4504-10.

[9] Barnes W M. PCR amplification of up to 35-kb DNA with high fidelity and high yield from λ bacteriophage templates. Proc Natl Acad Sci USA 1994; 91:2216-2220.

[10] Holden J F, Takai K, Summit M, Bolton S, Zyskowski J, Baross J A. Diversity among three novel groups of hyperthermophilic deep-sea *Thermococcus* species from three sites in the northeastern Pacific Ocean. FEMS Microbiol Ecol 2001; 36:51-60.

[11] Robb F T, Place A R, Sowers K R, Schreier H J, DasSarma S, Fleischmann, E M. Archaea: A Laboratory Manual. Cold Spring Harbor Laboratory Press, Cold Spring Harbor, N.Y. 1995.

[12] Sambrook J, Russell D W. Molecular cloning: a laboratory manual, $3^{rd}$ ed. Cold Spring Harbor Laboratory, Cold Spring Harbor, N.Y. 2001.

[13] Bradford M M. A rapid and sensitive method for the quantitation of microgram quantities of protein utilizing the principle of protein-dye binding. Anal Biochem 1976; 72:248-254.

[14] Laemmli U K. Cleavage of structural proteins during the assembly of the head of bacteriophage T4. Nature 1970; 227:680-685.

[15] Choi J J, Kwon S-T. Cloning, expression, and characterization of DNA polymerase from hyperthermophilic bacterium *Aquifex pyrophilus*. J Microbiol Biotechnol 2004; 14:1022-1030.

[16] Kahler M, Antranikian G. Cloning and characterization of family B DNA polymerase from the hyperthermophilic crenarchaeon *Pyrobaculum islandicum*. J Bacteriol 2000; 182:655-663.

[17] Hodges R A, Perler F B, Noren C J, Jack W E. Protein splicing removes intervening sequences in an archaea DNA polymerase. Nucleic Acids Res 1992; 20:6153-6157.

[18] Perler F B, Olsen G J, Adam E. Compilation and analysis of intein sequences. Nucleic Acids Res 1997; 25: 1087-1093.

[19] Studier F W, Moffatt B A. Use of bacteriophage T7 RNA polymerase to direct selective high-level expression of cloned genes. J Mol Biol 1986; 189: 113-130.

[20] Lecompte O, Ripp R, Puzos-Barbe V, Duprat S, Heilig R, Dietrich J, Thierry J C, Poch O Genome evolution at the genus level: comparison of three complete genomes of hyperthermophilic archaea. Genome Res 2001; 11:981-93.

[21] Fukui T, Atomi H, Kanai T, Matsumi R, Fujiwara S, Imanaka T. Complete genome sequence of the hyperthermophilic archaeon *Thermococcus kodakaraensis* KOD1 and comparison with *Pyrococcus* genomes. Genome Res 2005; 15:352-363.

[22] Nishioka M, Mizuguchi H, Fujiwara S, Komatsubara S, Kitabayashi M, Uemura H, Takagi M, Imanaka T. Long and accurate PCR with a mixture of KOD DNA polymerase and its exonuclease deficient mutant enzyme. J Biotechnol 2001; 88:141-149.

TECHNICAL PROBLEM

It is an object of the present invention to provide a hyperthermophilic DNA polymerase having high fidelity and elongation ability.

Another object of the present invention is to provide a method for producing a hyperthermophilic DNA polymerase having high fidelity and elongation ability.

TECHNICAL SOLUTION

The present invention provides a DNA polymerase and a preparation method thereof. The preparation method is preferably carried out using a genetic engineering method, but is not limited thereto.

Also, the present invention provides an isolated DNA sequence encoding said DNA polymerase, and a recombinant vector containing said DNA sequence.

ADVANTAGEOUS EFFECTS

The DNA polymerase according to the present invention is a novel DNA polymerase, which is hyperthermophilic and has an elongation ability and fidelity higher than those of prior commercial DNA polymerases. Thus, the DNA polymerase according to the present invention will be useful in precision analysis, precision diagnosis, identification and the like, which require accurate PCR.

BRIEF DESCRIPTION OF THE DRAWINGS

FIG. 1 shows the comparison of amino acid sequence of family B-type DNA polymerase from *Thermococcus* sp. NA1 (TNA1; SEQ ID NO: 2), *T. kodakarensis* KOD1 (TkKOD1, gi:52696275; SEQ ID NO: 17), *Pyrococcus furiosus* (Pfu, gi:18892147; SEQ ID NO: 18), and *Pyrococcus* sp, GB-D (PGBD, gi:436495; SEQ ID NO: 19). In FIG. 1, the dashes (-) represent gaps, and numerals on the right side represent the numbers of last residues in original sequences. The same residue between four enzymes is indicated as "*", and conservatively substituted residues and semi-conservatively substituted residues are indicated as ":". In a range from Pol I to Pol IV, a region conserved in family B DNA polymerase is shown; in a range from Exo I to Exo III, a conserved motif of a 3'->5' exonuclease domain is shown; and a DNA-binding motif is shown.

In FIG. 2, M: a standard sample; 2: a crude extract; 3: His-tagged affinity chromatography after heat treatment. The molecular weight standard sample (lane M) contained phosphorylase b (103 kDa), bovine serum albumin (77 kDa), ovalbumin (50 kDa), carbonic anhydrase (34.3 kDa), soybean trypsin inhibitor (28.8 kDa), and lysozyme (20.7 kDa).

In FIG. 4, (A): the effect of temperature on DNA polymerase activity; and (B): the thermal stability of TNA1_pol. Recombinant TNA1_pol was pre-incubated at 95° C. (▲) and 100° C. (•), and the remaining activity was measured at 75° C.

In FIG. 7(A), lane M: DNA molecular size marker; lane 1: negative control group; lane 2: Ex Taq DNA polymerase (TaKaRa); lane 3: Pfu Turbo DNA polymerase (Stratagene); lane 4: KOD DNA polymerase (Novagen); lane 5: TNA1-pol. In FIG. 7(B), lane M: DNA molecular size marker; lane 1: 2-kb PCR amplification; lane 2: 4-kb PCR amplification; lane 3: 8-kb PCR amplification. The PCR reaction with TNA1-pol were conducted in 20 mM Tris-HCl (pH 8.5), 30 mM $(NH_4)_2SO_4$, and 1 mM $MgCl_2$, and PCR amplification reactions with other commercial polymerases were carried out according to standard protocols recommended by the manufacturers.

BEST MODE FOR CARRYING OUT THE INVENTION

Figure 2:
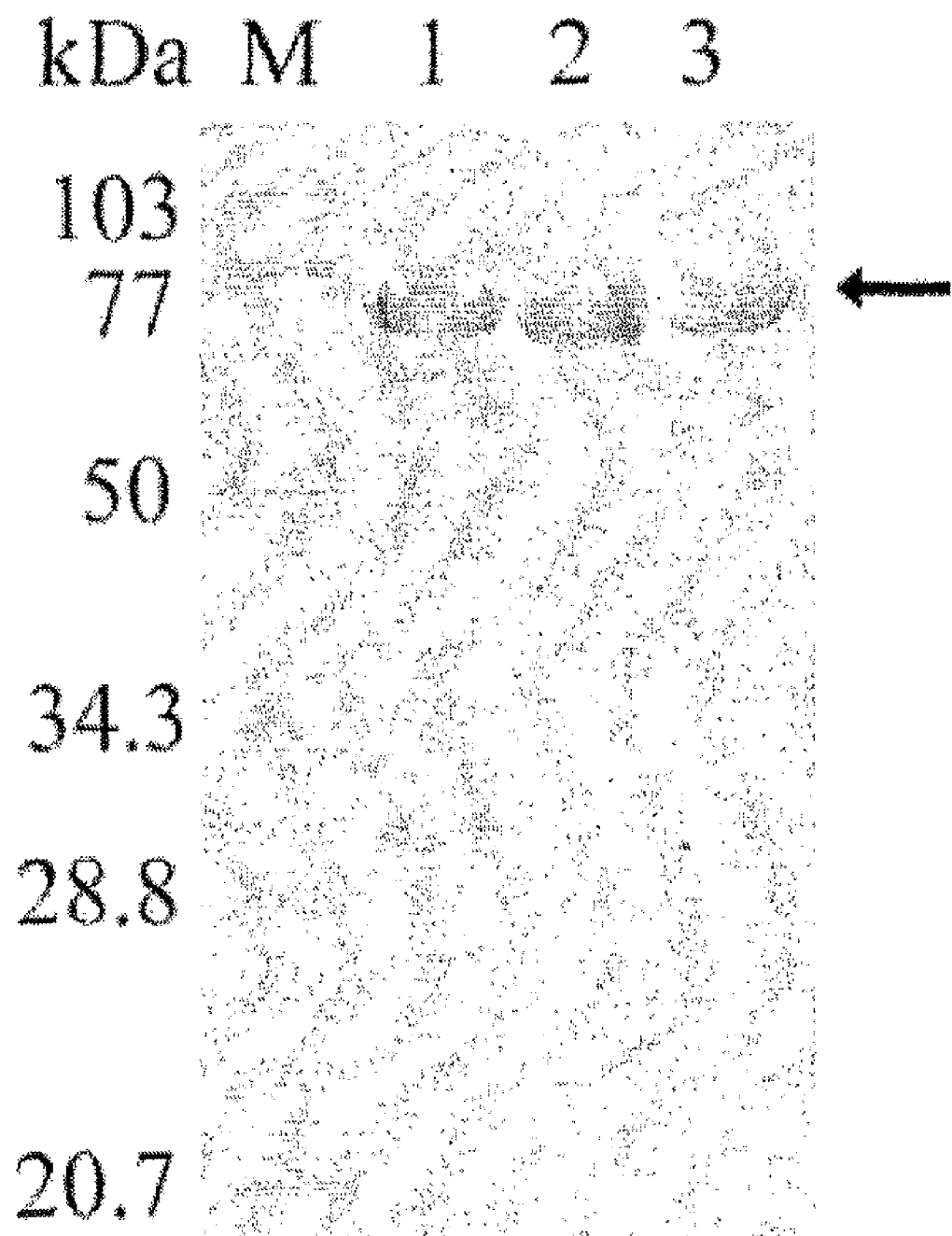
FIG. 2 shows the results of SDS-PAGE analysis of TNA1-pol.

The present invention provides a DNA polymerase and a preparation method thereof. The preparation method is preferably conducted according to a genetic engineering method, but is not limited thereto.

Also, the present invention provides an isolated DNA sequence encoding said DNA polymerase, and a recombinant vector containing said DNA sequence.

According to a first aspect, the present invention provides a nucleic acid sequence encoding a DNA polymerase stable at high temperature, and a nucleic acid sequence equivalent to said sequence. More specifically, said nucleic acid sequence is shown in SEQ ID NO: 1.

As used herein, the term "DNA polymerase" refers to an enzyme that synthesizes DNA in the 5'->3' direction from deoxynucleotide triphosphate using a complementary template DNA strand and a primer by successively adding nucleotide to a free 3'-hydroxyl group. The template strand determines the sequence of the added nucleotide by Watson-Crick base pairing.

As used herein, the term "equivalent nucleic acid sequence" is intended to include the degenerate codon sequence of said DNA polymerase sequence.

As used herein, the term "degenerate codon sequence" refers to a nucleic acid sequence, which is different from said naturally occurring sequence, but encodes a polypeptide having the same sequence as that of the naturally occurring DNA polymerase disclosed in the present invention.

According to a second aspect, the present invention provides a DNA polymerase. More particularly, the present invention provides a DNA polymerase shown in SEQ ID NO: 2, and a functional equivalent thereof.

As used herein, the term "functional equivalent" is intended to include amino acid sequence variants having amino acid substitutions in some or all of a DNA polymerase of SEQ ID NO: 2, or amino acid additions or deletions in some of the DNA polymerase. The amino acid substitutions are preferably conservative substitutions. Examples of the conservative substitutions of naturally occurring amino acids include aliphatic amino acids (Gly, Ala, and Pro), hydrophobic amino acids (Ile, Leu, and Val), aromatic amino acids (Phe, Tyr, and Trp), acidic amino acids (Asp, and Glu), basic amino acids (His, Lys, Arg, Gln, and Asn), and sulfur-containing amino acids (Cys, and Met). The deletions of amino acids are located in a region which is not involved directly in the activity of the DNA polymerase.

According to a third aspect, the present invention provides a recombinant vector comprising an isolated DNA fragment encoding said DNA polymerase.

As used herein, the term "vector" means a nucleic acid molecule that can carry another nucleic acid bound thereto. As used herein, the term "expression vector" is intended to include a plasmid, cosmid or pharge, which can synthesize a protein encoded by a recombinant gene carried by said vector. A preferred vector is a vector that can self-replicate and express a nucleic acid bound thereto.

According to a fourth aspect, the present invention provides cells transformed with said recombinant vector.

As used herein, the term "transformation" means that foreign DNA or RNA is absorbed into cells to change the genotype of the cells.

Cells suitable for transformation include prokaryotic, fungal, plant and animal cells, but are not limited thereto. Most preferably, *E. coli* cells are used.

According to a fifth aspect, the present invention provides a method for producing a DNA polymerase using said transformed cells or *Thermococcus* sp.

Hereinafter, the present invention will be described in further detail with reference to examples. It is to be understood, however, that these examples are for illustrative purposes only and are not to be construed to limit the scope of the present invention.

MODE FOR CARRYING OUT THE INVENTION

EXAMPLE 1

Cloning and Primary sequence analysis of TNA1 pol gene

*Thermococcus* sp. NA1 was isolated from deep-sea hydrothermal vent area at the PACMANUS field (3° 14' S, and 151° 42' E) in East Manus Basin. An YPS medium [see reference 10] was used to culture *Thermococcus* sp. NA1 for DNA manipulation, and the culture and maintenance of *Thermococcus* sp. NA1 were conducted according to standard methods [see reference 11]. To prepare a *Thermococcus* sp. NA1 seed culture, an YPS medium in a 25-ml serum bottle was inoculated with a single colony formed on a phytagel plate, and cultured at 90° C. for 20 hours. The seed culture was used to inoculate 700 ml of an YPS medium in an anaerobic jar, and was cultured at 90° C. for 20 hours.

Preparation of mature TNA1-pol gene *E. coli* DH5α was used for plasmid propagation and nucleotide sequence analysis. *E. coli* BL21-Codonplus(DE3)-RIL cells (Stratagene, La Jolla, Calif.) and plasmid pET-24a(+) (Novagen, Madison, Wis.) were used for gene expression. The *E. coli* strain was cultured in a Luria-Bertani medium at 37° C., and kanamycin was added to the medium to a final concentration of 50 µg/ml.

DNA manipulation was conducted according to a standard method as described by Sambrook and Russell [see reference 11]. The genomic DNA of *Thermococcus* sp. NA1 was isolated according to a standard method [see reference 11]. Restriction enzymes and other modifying enzymes were purchased from Promega (Madison, Wis.). The preparation of a small scale of plasmid DNA from the *E. coli* cells was performed using the plasmid mini-kit (Qiagen, Hilden, Germany). The sequence analysis of DNA was performed with an automated sequencer (ABI3100) using the BigDye terminator kit (PE Applied Biosystems, Foster City, Calif.).

Figure 1:
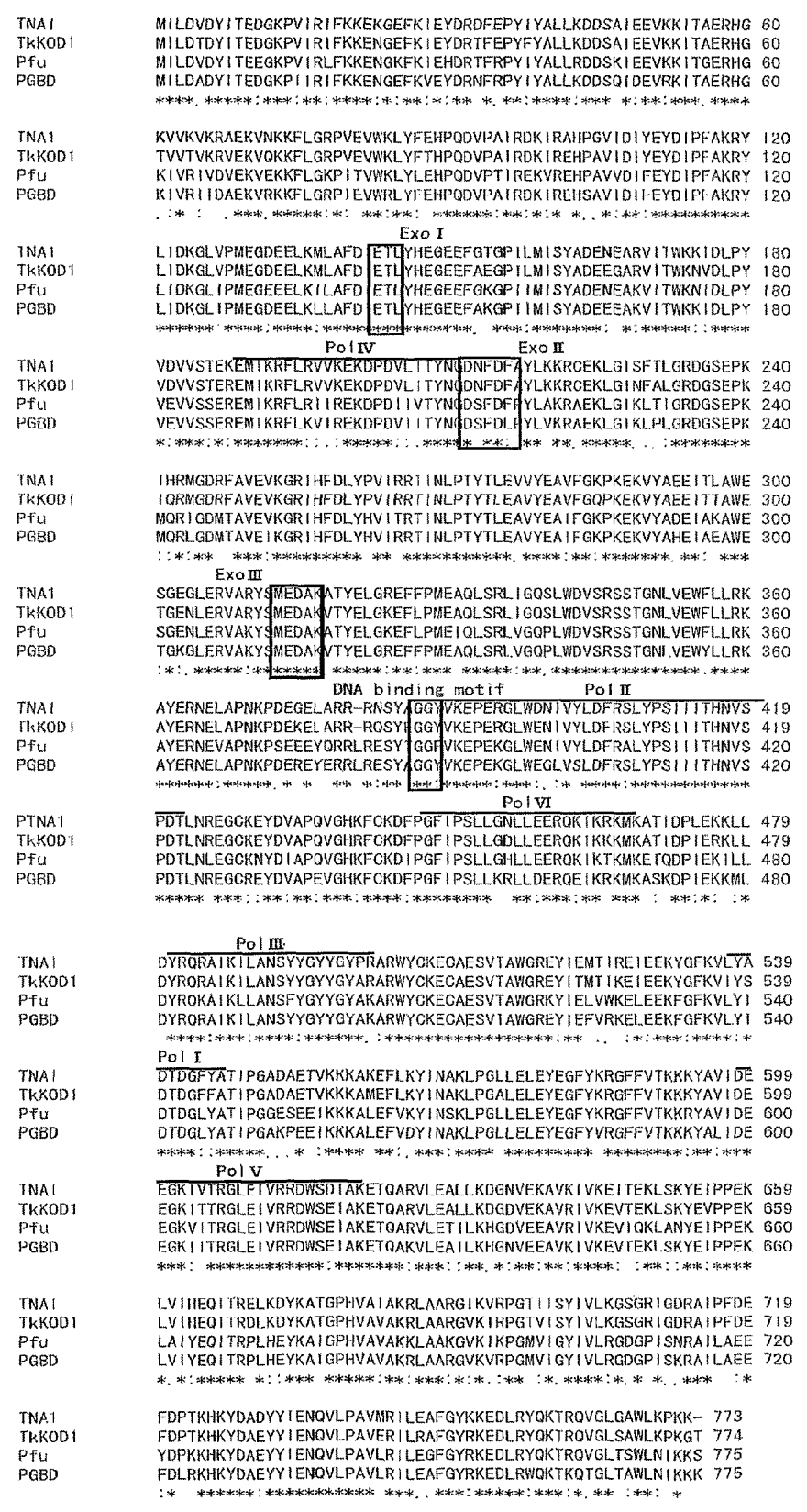

Through the genomic sequence analysis, an open reading frame (3,927 bp; SEQ ID NO: 3) encoding a protein consisting of 1,308 amino acids was found, and it showed a very high similarity to the family B DNA polymerases. The molecular mass of a protein derived from the deduced amino acid sequence (SEQ ID NO: 4) was 151.9 kDa, which was much larger than the size predicted for the average molecular mass thermostable DNA polymerases. The sequence analysis showed that the DNA polymerase gene contained a putative 3'-5' exonuclease domain, an α-like DNA polymerase domain, and a 1605-bp (535 amino acids) in-frame intervening sequence in the middle of a region (Pol III) conserved between the α-like DNA polymerases of eukaryotes and archaeal (Pol III) (see FIG. 1 and reference 16). Also, the deduced amino acid sequence of the intein of the polymerase was highly similar to the intein of the polymerase of other archaeal, and exhibited a identity of 81.0% to a pol_1 intein 1 (derived from a DNA polymerase of *Thermococcus* sp. strain GE8; 537 amino acids; AJ25033), a identity of 69.0% to IVS-B (derived from KOD DNA polymerase; 537 amino acids; D29671) and a homology of 67.0% to an intein (derived from deep vent DNA polymerase; 537 amino acids; U00707).

The splicing site of the intein could be predicted by sequence analysis, because Cys or Ser was well conserved in the N-terminus of the intein, and His-Asn-Cys/Ser/Thr was well conserved in the C-terminal splice junction [see references 17 and 18]. Thus, a mature polymerase gene (TNA1_pol) containing no intein could be predicted, and it would be a 2,322-bp sequence (SEQ ID NO: 1) encoding a protein consisting of 773 amino acid residues (SEQ ID NO: 2). The deduced sequence of TNA1_pol was compared with those of other DNA polymerases (see FIG. 1). In pairwise alignment, the deduced amino acid sequence of the mature TNA1_pol gene showed a identity of 91.0% to KOD DNA polymerase (gi:52696275), a identity of 82.0% to deep vent DNA polymerase (gi:436495), and a identity of 79.0% to pfu DNA polymerase (gi:18892147). To examine the performance of TNA1_pol in PCR amplification, TNA1_pol DNA was pconstructed by removing the intein from the full-length polymerase as described above.

The mature DNA polymerase containing no intein was constructed in the following manner. Using primers designed to contain overlapping sequences, each of the TNA1-pol N-terminal region (sense [5'-CGACCCGGCATATGATC-CTCGACGTCGATTACATCACAG-3'] (SEQ ID NO: 5) and antisense [5'-GCCGTAGTACCCGTAATAGCTGTTCGCT-AAGATTTTTATTGCCCGCTG-3'] (SEQ ID NO: 6)) and C-terminal portion (sense [5'-CAGCGGGCAATAAAA-ATCTTAGCGAACAGCTATTACGGGTACTACGGC-3'] (SEQ ID NO: 7) and antisense [5'-CTCCACATCTC-GAGTTTCTTC GGCTTCAACCAAGCCCC-3'] (SEQ ID NO: 8)) was amplified. Then, the full length of a TNA1_pol gene flanked by NdeI and XhoI sites was amplified by PCR using two primers (sense [5'-CGACCCGGCATATGATC-CTCGACGTCGATTAC ATCACAG-3'] (SEQ ID NO: 9) and antisense [5'-CTCCACATCTCGAGTTTCTTCGGCTTCA-ACCAAGCCCC-3'] (SEQ ID NO: 10)) and a mixture of said partially PCR amplified N-terminal and C-terminal fragments as a template. The amplified fragment was digested with NdeI and XhoI, and ligated with pET-24a(+) digested with NdeI/XhoI. The ligate was transformed into *E. coli* DH5α. Candidates having a correct construct were selected by restriction enzyme digestion, and were confirmed to have a mature DNA polymerase by analyzing the DNA sequence of the clones.

EXAMPLE 2

Expression and Isolation of TNA1-pol

The pET system having a very strong, stringent T7/lac promoter, is one of the most powerful systems developed for the cloning and expression of a heterologus proteins in *E. coli* [see reference 19], and the TNA1_pol gene was amplified and inserted into the NdeI and XhoI sites of pET-24a(+) in order to facilitate the over-expression of TNA1-pol and the His-tagged purification of recombinant TNA1-pol. The resulting expression plasmid was designated as pETNAPm. The recombinant TNA1_pol was expressed in a soluble form in the cytosol of *E. coli* BL21-codonPlus(DE3)-RIL harbourng pETNAPm.

The above-prepared expression plasmid, pETNAPm, was transformed into *E. Coli* BL21-CodonPlus(DE3)-RIL. The overexpression of the TNA1_pol gene was induced by adding isopropyl-β-D-thiogalactopyranoside (IPTG) in the mid-exponential growth stage, followed by constant-temperature incubation at 37° C. for 3 hours. The cells were harvested by centrifugation (at 4° C. and 6,000×g for 20 minutes), and re-suspended in a 50 mM Tris-HCl buffer (pH 8.0) containing 0.1M KCl and 10% glycerol. The cells were ultrasonically disrupted, and isolated by centrifugation (at 4° C. and 20,000×g for 30 minutes), and a crude enzyme sample was thermally treated at 80° C. for 20 minutes. The resulting supernatant was treated in a column of TALON™ metal affinity resin (BD Bioscience Clontech, Palo Alto, Calif.), and washed with 10 mM imidazole (Sigma, St. Louis, Mo.) in a 50 mM Tris-HCl buffer (pH 8.0) containing 0.1 M KCl and 10% glycerol, and TNA1_pol was eluted with 300 mM imidazole in buffer. The pooled fractions were dialyzed into a storage buffer containing 50 mM Tris-HCl (pH 7.5), 1 mM DTT, 1 mM EDTA and 10% glycerol.

The concentrations of proteins were determined by the colorimetric assay of Bradford [see reference 13]. The purification degrees of the proteins were examined by sodium dodecyl sulfate-polyacrylamide gel electrophoresis (SDS-PAGE) analysis according to a standard method [see reference 14].

As shown in FIG. 2, the thermal treatment conducted at 80° C. for 20 minutes could eliminate effectively several *E. coli* proteins. However, some *E. Coli* proteins remained in a stable form after the thermal treatment. The soluble supernatant of the heat-treated pool was chromatographied on a column of TALON™ metal affinity resin, and purified as shown in Table 1 and FIG. 2. The specific activity of the purified protein was 231.33 units/mg, and the purification yield was 26.155%. SDS-PAGE analysis revealed a major protein band with a molecular mass of 80 kDa. The purified proteins remained soluble in repeated freezing and thawing cycles.

TABLE 1

Isolation of TNA1_pol from *E. coli*

| Purification step | Total protein (mg) | Total activity (U) | Specific activity (U/mg) | Yield (%) |
|---|---|---|---|---|
| Crude extract | 46.6 | 2915.26 | 62.62 | 100 |
| Thermal denaturation | 29.7 | 2518.62 | 127.85 | 36.31 |
| His-tagged affinity column | 3.3 | 763.37 | 231.33 | 26.15 |

EXAMPLE 3

Properties of TNA-pol

Analysis of DNA Polymerase Activity

The DNA polymerase activity of the purified enzyme was measured according to some modifications of the method described by Choi and Kwon [see reference 15]. The enzyme was incubated in a reaction mixture (25 µl) consisting of 20 mM Tris-HCl (pH 7.5), 10 mM $MgCl_2$, 1 mM 2-mercaptoethanol, 100 µM of each of dATP, dCTP and dGTP, 0.25 µCi of [methyl-$^3$H]thymidine 5'-triphosphate, and 625 ng of activated calf thymus DNA (Promega) at 75° C. for 10 minutes. The reaction was stopped on ice, and an aliquot was spotted onto a DE81 filter paper disc (23 mm, Whatman, UK). The disc was dried on a heat block, and washed in 0.5 M sodium phosphate buffer (pH 7.0) for 10 minutes and 70% ethanol for 5 minutes, followed by drying. The incorporated radioactivity of the dried filter paper disc was counted using a Beckman LS6500 scintillation counter (USA). One unit of TNA1_pol is defined as the amount of polymerase that incorporates 1 pmole of [$^3$H]TTP into an acid-insoluble product at 75° C. for 1 minute.

Exonuclease Activity Analysis

To prepare a 3' end-labeled DNA substrate, pBluescript SK-DNA linearized by Not I was filled by a Klenow fragment in the presence of [α-$^{32}$P]dCTP. To prepare a 5' end-labeled DNA substrate, a 2-kb PCR product was phosphorylated by T4 polynucleotide kinase in the presence of [γ-$^{32}$P]ATP. After labeling, each of the DNA substrate was purified by ethanol precipitation. For endonuclease activity assay, each of the DNA substrate was incubated with the enzyme in a reaction mixture (25 µl) consisting of 20 mM Tris-HCl (pH 7.5), 10 mM $MgCl_2$, 1 mM 2-mercaptoethanol, 20 mM $(NH_4)_2SO_4$ and 0.01% BSA at 75° C. for 10 minutes in the presence or absence of dNTPs. The reaction was stopped on ice, and precipitated by adding 1 ml of 5% trichloroacetic acid in the presence of BSA as a carrier. After centrifugation, the supernatant was withdrawned and the radioactivity thereof was counted using a Beckman LS6500 scintillation counter (USA).

Figure 3:
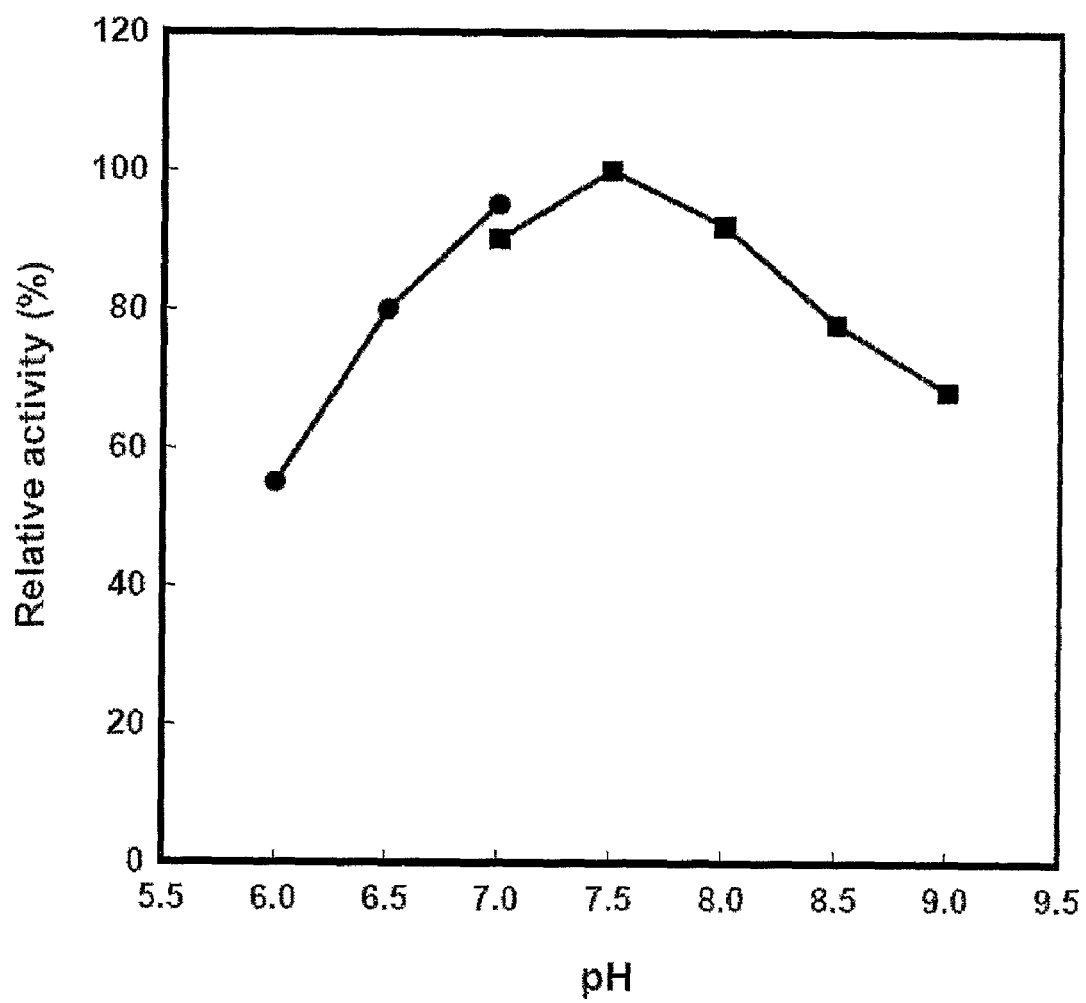
FIG. 3 shows the effect of pH on the DNA polymerase activity of TNA1-pol. The analysis of activity was conducted in the following buffers (each 50 mM) using a standard method: MES, pH 6.0-7.0; Tris-HCl, pH 7.0-9.0; and glycine, pH 9.0-10.0.
Figure 4:
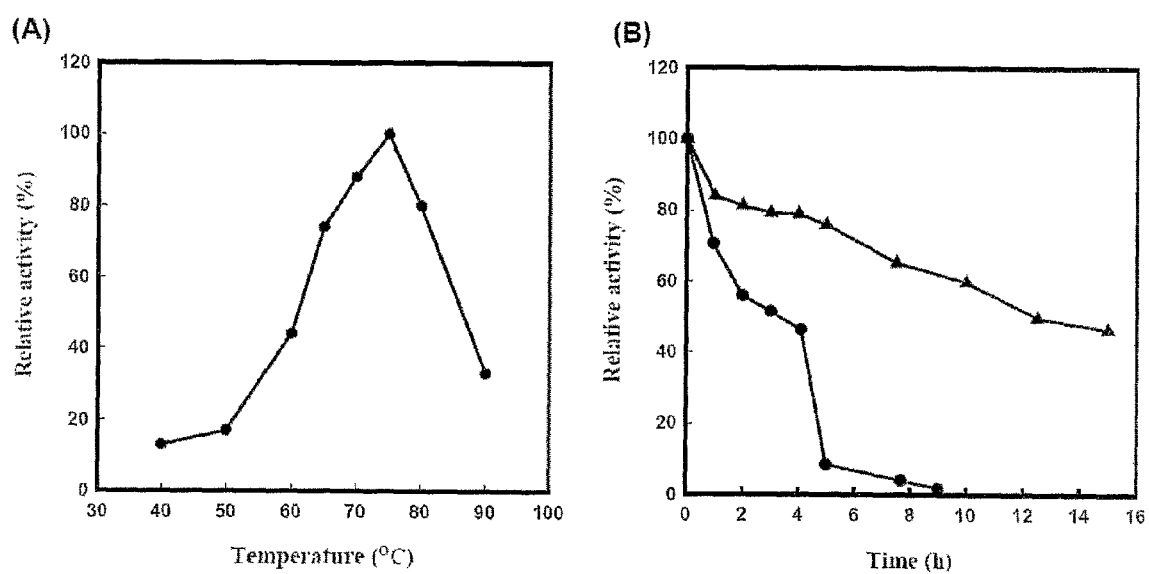
FIG. 4 shows the effects of temperature on the DNA polymerase activity and thermal stability of TNA1-pol.

The pH dependency of TNA1-pol was examined in the range of pH 6.0-10.0. The optimal activity occurred at pH 7.5 (see FIG. 3). The dependency of the polymerase activity on temperature was determined in the temperature range of 40-90° C., and the optimal activity of TNA1_pol ouccurred at 75° C. in analysis conducted using a activated calf thymus DNA template (see FIG. 4A). Because the TNA1_pol was thermally stable at 95° C. as described below, the optimal temperature thereof was influenced by the denaturation of the bovine thymus DNA template at 75° C. or higher. The thermal stability if TNA1_pol was tested by measuring the activity of the polymerase at 95° C. and 100° C. after pre-incubation. The half-life ($t_{1/2}$) of the enzyme was 3.5 hours at 100° C. ($t_{1/2}$), and 12.5 hours at 95° C. ($t_{1/2}$) (see FIG. 4B).

Figure 5:
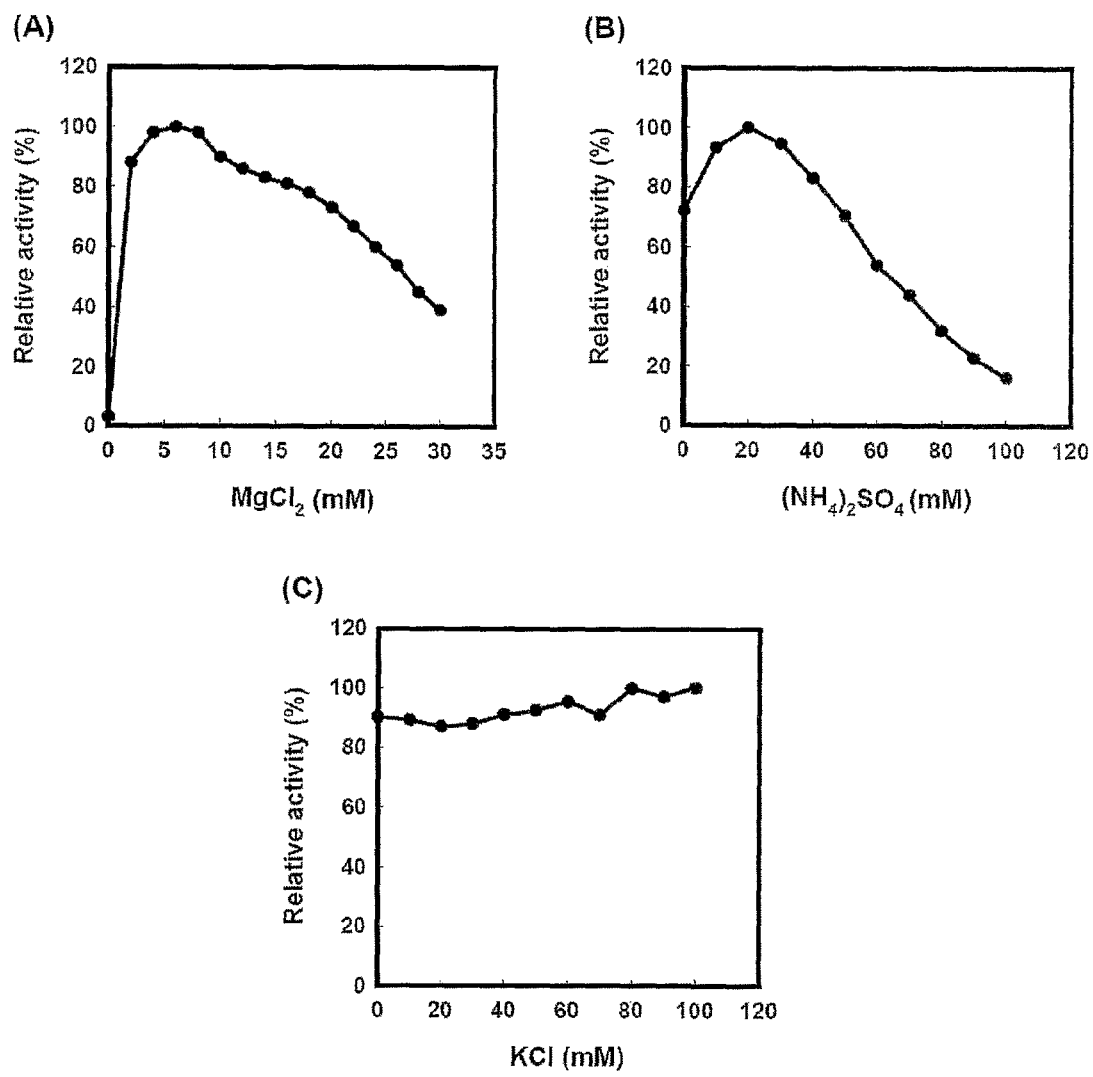
FIG. 5 shows the effects of magnesium ions (A), ammonium ions (B) and potassium ions (C) on the DNA polymerase activity of TNA1-pol. The analysis of activity was conducted in the presence of $MgCl_2$, $(NH_4)_2SO_4$, and KCl.

The effects of concentrations of $MgCl_2$, $(NH_4)_2SO_4$ and KCl on the activity of TNA1_pol were examined (see FIG. 5). TNA1_pol was dependent on the presence of $MgCl_2$, showed the maximal activity at a 6 mM $MgCl_2$ concentration. These results were consistent with the effects of cations on other DNA polymerases [see reference 15]. Most DNA binding enzymes, including DNA-dependent DNA polymerases, tend to prefer the presence of $Mg^{2+}$ ion. It is noticeable that the optimal concentration of $Mg^{2+}$ ions for the activity of polymerases can differ from the optimal concentration for PCR amplification, and the practical amplification of TNA1_pol was performed at a significantly low $Mg^{2+}$ concentration. The optimal concentration of $(NH_4)SO_4$ was determined to be 20 mM, but KCl had no great effect on the activity of TNA1_pol (see FIGS. 5B and C).

EXAMPLE 4

Exonuclease Activity of TNA1_pol

Figure 6:
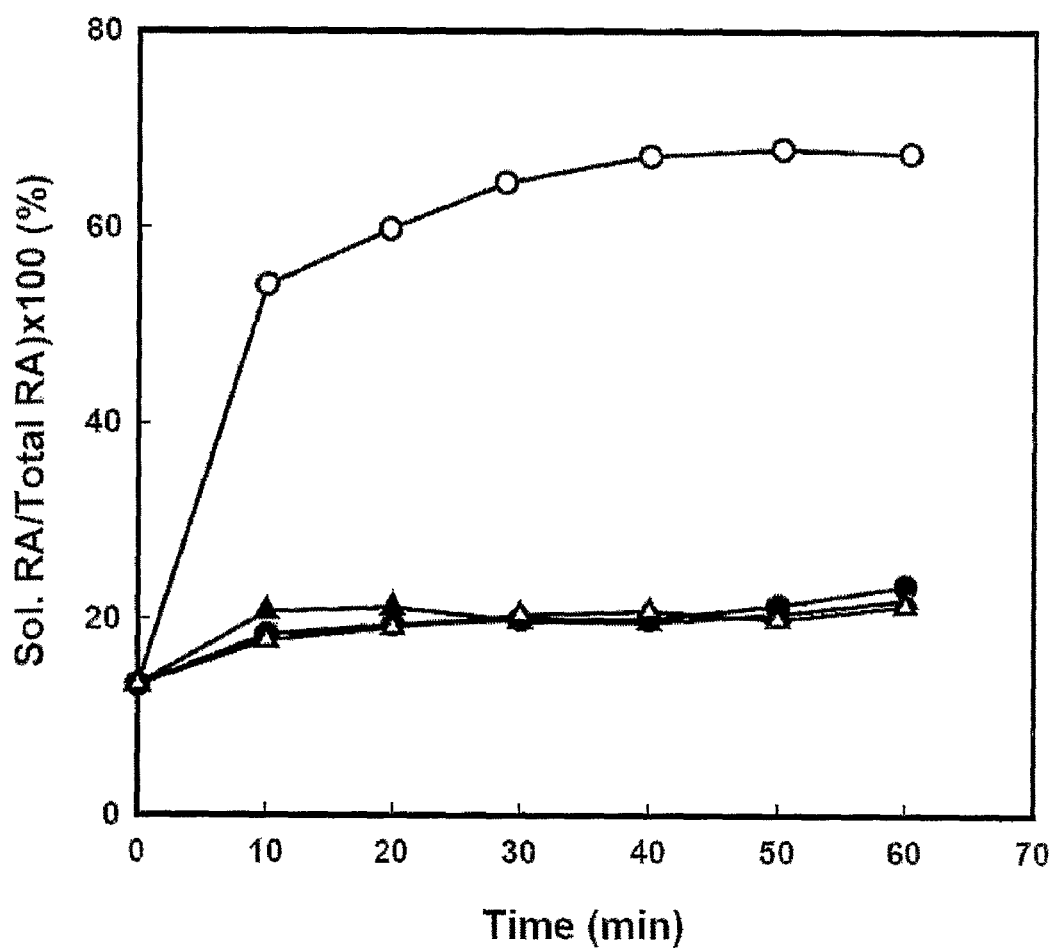
FIG. 6 shows the results of exonuclease activity of recombinant TNA_pol. The activity of 3'->5' exonuclease was analyzed in the absence (○) or presence (•) of dNTP. The activity of 5'-3' exonuclease was analyzed in the absence (Δ) or presence (▲) of dNTP.

The sequence analysis of TNA1_pol gene showed the presence of the putative 3'->5' exonuclease domains (ExoI, ExoII, and ExoIII), implicating that TNA1_pol would have associated 3'->5' exonuclease. To address the issue, the activities of 3'->5' and 5'->3' exonucleases of TNA1_pol were quantified by measuring the release of $^{32}P$ from the 3' and 5' end-labeled DNA substrates. As a result, 68% of $^{32}P$ was released from the TNA1_pol 3 end-labeled DNA within one hour, but the release of $^{32}P$ from the 5 end-labeled DNA was very low and was not increased with dNTP (FIG. 6). This suggests that TNA1_pol had 3'->5' exonuclease activity which would be supported by the domain structure consisting of three motifs (ExoI, ExoII, and ExoIII). However, it had no 5'->3' exonuclease activity. Almost all of archaeal family B type DNA polymerases are known to possess associated 3'->5' exonuclease activity [see reference 16].

The comparative genomic analysis of closely related hyperthermophilic species of archaea belonging to the family Thermococcales disclosed a high genomic plasticity comparable to plasticity observed between closely related bacteria [see references 20 and 21]. Furthermore, the comparison between protein profiles related that high amounts of differential gains and losses occurred, and the polymorphisms in such species would probably be associated with the fact that these freely living organisms adapted themselves to other environmental constrains. Nevertheless, orthologous gene groups conserved in the hyperthermophilic archaea species indicated that DNA polymerases having high 3'->5' proof-reading exonuclease activity was necessary for minimizing severe mutations in a core gene crucial for the survival of hyperthermophilic bacteria against strong evolutionary pressure.

EXAMPLE 5

PCR with TNA1_pol

The major application of thermostable DNA polymerases is the in vitro amplification of DNA fragments. To test the performance of recombinant TNA1_pol for in vitro amplification, said enzymes was applied to PCR reaction.

PCR amplification with recombinant TNA1-pol was attempted, and compared with PCR amplification reactions of commercial Ex Taq (TaKaRA), pfu Turbo (Stratagene) and KOD (Novagen) DNA polymerases. 2.5 U of each of various DNA polymerases was added to 50 µl of a reaction mixture containing 50 ng of genomic DNA from *Thermococcus* sp. NA1 as a template, 10 pmole of each of primers, 200 µM dNTP, and PCR reaction buffer. To amplify a 2-kb fragment from the genomic DNA of *Thermococcus* sp. NA1, primers [sense 5'-ACTAAATTGGTGATACCGTTATGAG-3' (SEQ ID NO: 11) and antisense 5'-GGAACATAAAATGTAAGG-GACTTC-3' (SEQ ID NO: 12)] were designed. PCR buffer supplied by the manufacturer was used in the amplification of the commercial polymerases. Also, for the PCR amplification of recombinant TNA1_Pol, a buffer consisting of 20 mM Tris-HCl (pH 8.5), 30 mM $(NH_4)_2SO_4$, 60 mM KCl and 1 mM $MgCl_2$ was used. The PCR reaction was performed in the following conditions: a single denaturation step at 95° C., and then 30 cycles with a temperature profile of 1 min at 94° C., 1 min at 55° C. and 2 min at 72° C., followed by final extension for 7 min at 72° C. The PCR products were analyzed in 0.8% agarsose gel electrophoresis. To test the performance of recombinant TNA1_pol on the amplification of long-chain DNA, PCR reaction was carried out in 50 µl of a reaction mixture containing 50 ng of genomic DNA from *Thermococcus* sp. NA1 as a template, 200 µM dNTP, and PCR reaction buffer. Primers were designed to amplify a 2 kb DNA fragment, a 4 kb DNA fragment [(sense 5'-ACTAAATTGGT-GATA CCGTTATGAG-3' (SEQ ID NO: 13) and antisense 5'-GTCTCTGATGCTCATGATGTAGTTC-3' (SEQ ID NO: 14)], and a 8 kb DNA fragment [sense 5'-ACTAAATTGGT-GATACCGTTATGAG-3' (SEQ ID NO: 15) and antisense 5'-GAGGAGCT CTTTAGATTCTCAAGC-3' (SEQ ID NO: 16)], from *Thermococcus* sp. NA1 (DQ223723).

Figure 7:
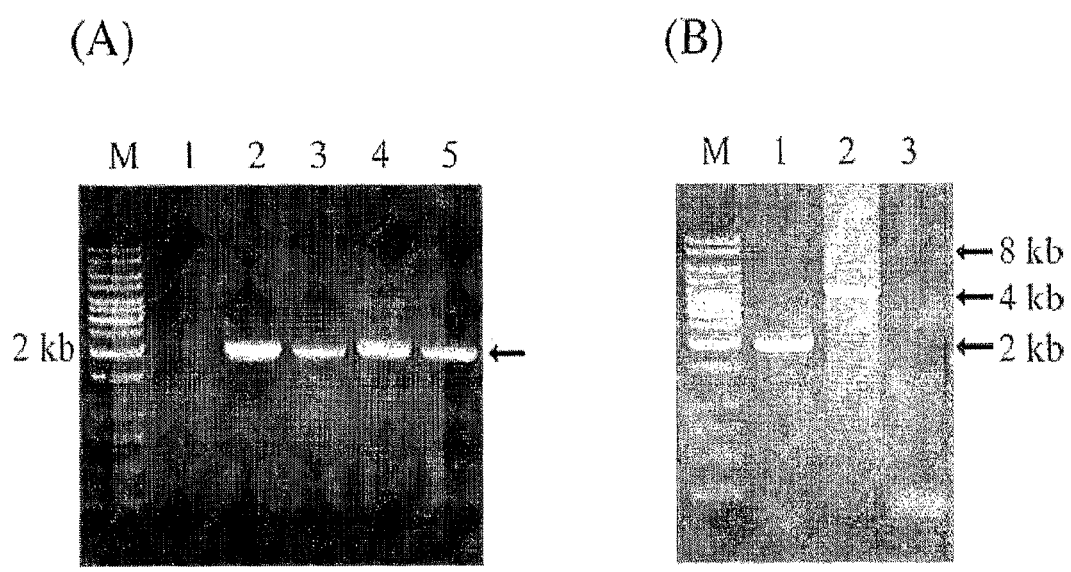
FIG. 7(A) shows the results of PCR amplification with various DNA polymerases.
FIG. 7(B) shows the results of amplification of a long-chain DNA fragment with TNA1-pol.
Figure 8:
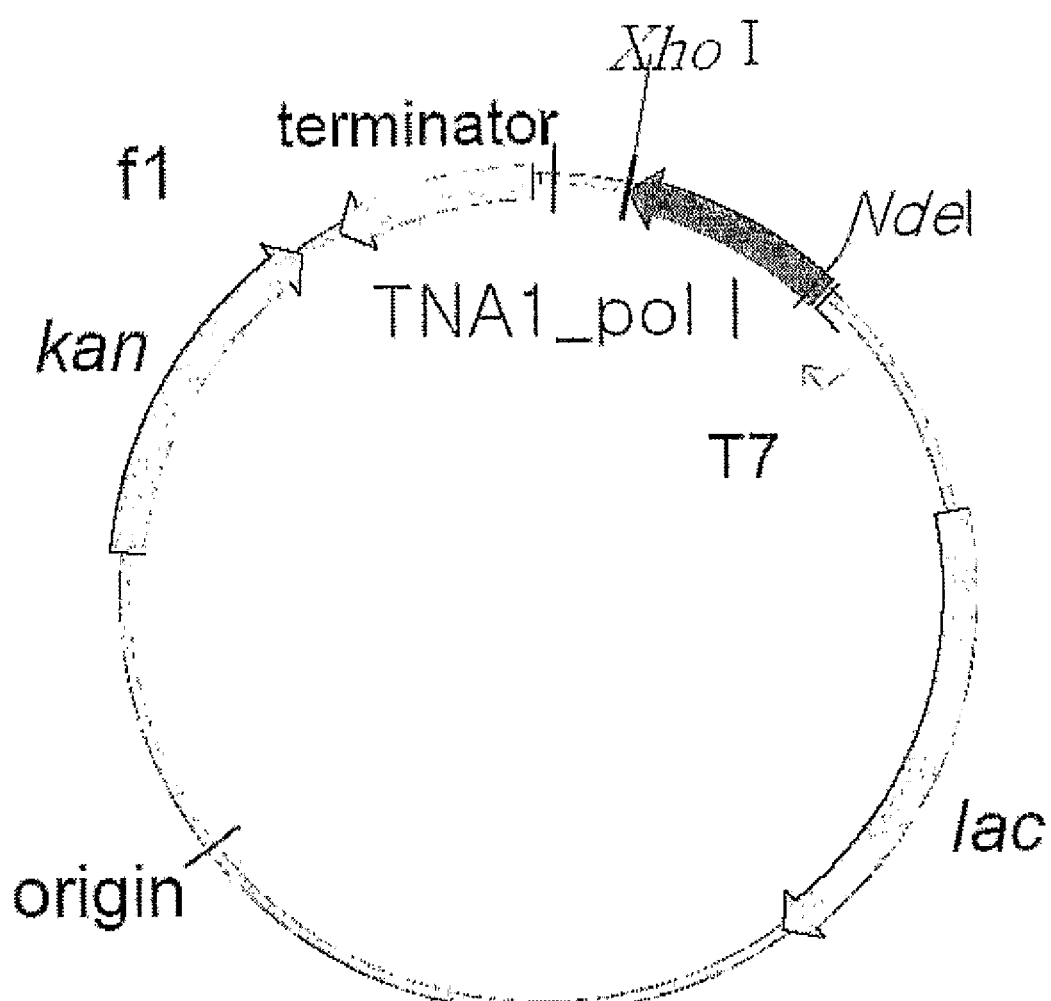
FIG. 8 shows a cleavage map of a pETNAPm recombinant plasmid having recombinant DNA polymerase TNA1-pol according to the present invention.

As shown in FIG. 7A, TNA1_pol successfully amplified the 2 kb target gene, and the PCR amplification yield thereof was comparable to those of Ex Taq, Pfu and KOD polymerases performed in their own PCR buffers supplied by the manufacturers, implicating that, when TNA1_pol is optimized, it will be industrially highly valuable (see FIG. 7A). Interestingly, practical pH for PCR amplification appeared to be different from optimal pH for the polymerase activity of TNA1_Pol. The in vitro amplification of DNA fragments is thought to be dependent on the balance between exonuclease activity and polymerase activity in the case of high-fidelity DNA polymerases. It is recommended that other commercial high-fidelity DNA polymerases, such as Pfu DNA polymerase (pH 8.8), KOD DNA polymerase (pH 8.8) and vent DNA polymerase (pH 8.8), which are generally used in PCR, should carry out PCR reactions in the alkaline pH value. High-fidelity DNA polymerases were reported to be unsuitable for the amplification of long DNA fragments due to their strong exonuclease activity [see reference 9]. In order to test whether recombinant TNA1_pol can amplify longer DNA fragments, recombinant TNA1_pol was applied in PCR reactions such that it amplified longer DNA fragments using the genomic DNA of *Thermococcus* sp. NA1. As shown in FIG. 7B, TNA1_pol could amplify DNA fragments up to a size of 8 kb. However, the yield of the 8 kb DNA amplification was lower than that of a 4 kb or 2 kb DNA fragment. This suggests that a wild-type protein of TNA1_pol needs to be introduced with mutations in order to optimize PCR reaction or to amplify longer DNA fragments.

Generally, family B-type DNA polymerases from hyperthermophilic archaea have 3'->5' exonuclease activity, and offer the possibility to amplify DNA fragments with high fidelity. However, most of family B-type DNA polymerases having 3'->5' exonuclease activity were lower in DNA elongation activity than A-type DNA polymerases having no exonuclease activity. The shortcoming of DNA polymerases having associated 3'-5' exonuclease activity can be overcame by the optimization of reaction buffer, the construction of mutations of reducing exonuclease 3'->5' activity, or the use of a mixture of exonuclease activity-free DNA polymerase and highly proofreading DNA polymerase (see reference 22). In addition, it is noted that the PCR-inhibiting effects of various components in biological samples can be eliminated to some extent by the use of appropriate thermostable DNA polymerases among polymerases having slightly different properties. KOD DNA polymerase was successful in overcoming the shortcoming in high processivity and high extention rate. The test results of the present invention show that TNA1-pol maintains high fidelity and has extention rate comparable to that of KOD DNA polymerase.

Industrial Applicability

As described above, the DNA polymerase according to the present invention is a novel DNA polymerase, which is hyperthermophilic and has an elongation ability and fidelity higher than those of prior commercial DNA polymerases. Thus, the DNA polymerase according to the present invention will be useful in precision analysis, precision diagnosis, identification and the like, which require accurate PCR.

The invention claimed is:

1. An isolated protein having the amino acid sequence of SEQ ID NO: 2.

2. An isolated nucleic acid molecule comprising the sequence of SEQ ID NO: 1.

3. An isolated nucleic acid molecule comprising a sequence that encodes a hyperthermophilic DNA polymerase having the amino acid sequence of SEQ ID NO: 2.

* * * * *